(12) United States Patent
Serrano-Wu et al.

(10) Patent No.: US 6,436,930 B1
(45) Date of Patent: Aug. 20, 2002

(54) THIO DERIVATIVES OF SORDARIN AS ANTIFUNGAL AGENTS

(75) Inventors: Michael Serrano-Wu, Guilford; Xuhua Du, Cheshire; Neelakantan Balasubramanian, Madison; Denis R. St. Laurent, Newington, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/952,987

(22) Filed: Sep. 14, 2001

Related U.S. Application Data

(60) Provisional application No. 60/232,762, filed on Sep. 15, 2000.

(51) Int. Cl.[7] .................... C07D 315/00; C07D 295/84; A61K 31/5375
(52) U.S. Cl. .................... 514/231.2; 549/418; 549/419; 549/420; 548/240; 514/378; 514/455; 514/460; 544/231.2; 544/237.8
(58) Field of Search .................... 548/240, 243; 549/417, 418, 419; 514/378, 455, 460, 230.2, 237.8; 544/158

(56) References Cited

U.S. PATENT DOCUMENTS 5,854,280 A * 12/1998 Gomez et al. .............. 514/456
6,040,463 A * 3/2000 Balkovec et al. ........... 549/418
6,054,478 A * 4/2000 Martin et al. ............... 514/460

* cited by examiner

Primary Examiner—T. A. Sololu
Assistant Examiner—Kamal Saeed
(74) Attorney, Agent, or Firm—David M. Morse

(57) ABSTRACT

The present invention relates to antifungal compounds having the structural formula:

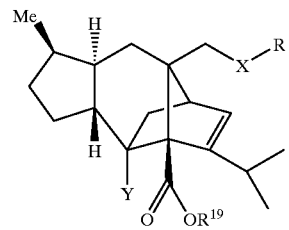

and pharmaceutically acceptable salts, solvates and prodrugs thereof. The present invention further relates to pharmaceutical compositions containing said compound, or a pharmaceutically acceptable salt, solvate or prodrug thereof, for use in the treatment of a fungal infection in an animal host.

20 Claims, No Drawings

THIO DERIVATIVES OF SORDARIN AS ANTIFUNGAL AGENTS

CROSS REFERENCE TO RELATED APPLICATION

This is a non-provisional application which claims the benefit of provisional application U.S. Ser. No. 60/232,762 filed Sep. 15, 2000.

BACKGROUND

Infections by *Candida albicans*, which include systemic, mucosal and cutaneous infections, are a common and often serious health problem.

*Candida albicans* is part of the normal flora of the skin, mucous membranes in the mouth, throat, intestine and genital tract. Normally Candida fungus lives in a healthy balance with the other bacteria and yeasts in the body as part of the normal flora.

However, a number of environmental stimuli can trigger the growth of Candida. Further, abnormal physiological changes in the epithelium may be involved together with a host of other factors, including genetics, nutrition, stress and other factors that result in infections of various organs of the body, particularly in immunosuppressed individuals or in individuals that have had the normal floral balance changed by the taking of wide spectrum antibiotics.

In addition, cancer patients, organ transplant patients and patients with immunologic disorders, chronic infections, leukemia, acquired immunodeficiency deficiency syndrome (AIDS), Hodgkin's disease, neutropenia and other hematologic diseases and endocrinopathies including diabetes are particularly susceptible to fungal infections by *Candida albicans*. Such immunologically compromised patients are at a risk of systemic candidiasis resulting from the inability of their immune system to destroy ubiquitous fungus of *Candida albicans* which is part of the normal environment. In fact, systemic candidiasis is one of the major causes of morbidity and mortality in immunocompromised individuals, particularly those patients who are neutropenic, suffering from AIDS, or who are undergoing immunosuppression for transplantation or therapy for cancer.

Recently, the incidence of serious, life-threatening, fungal infections has been increasing at an alarming rate. For example, the number of *Candida albicans* bloodstream infections in non-teaching hospitals increased by 370% between 1980 and 1990. At the same time the incidence of bloodstream infections by *C. albicans* in teaching hospitals increased by 487%. With the exception of coagulase negative staphylococci, statistically, *C. albicans* represents the fastest growing area of concern in hospital acquired bloodstream infections (Banejee et al., 1991, American Journal of Medicine 91 (3B): 86S-89S).

The natural product sordarin, its aglycone sordaricin, shown below

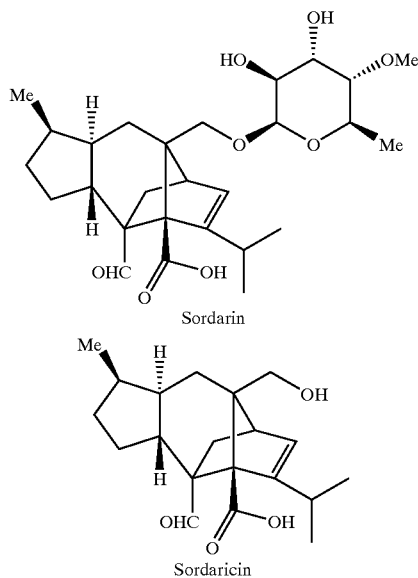

and its semi-synthetic derivatives have been discovered to selectively inhibit fungal protein synthesis. A broad spectrum of fungicidal activity has been demonstrated against a range of pathogens, and several sordarin derivatives have displayed excellent bioavailability and low mammalian toxicity.

Despite the prior identification of compounds having antifungal activity, what is needed are new compounds with improved activity against *Candida albicans*.

SUMMARY OF THE INVENTION

The present invention relates to antifungal compounds having the following structural formula:

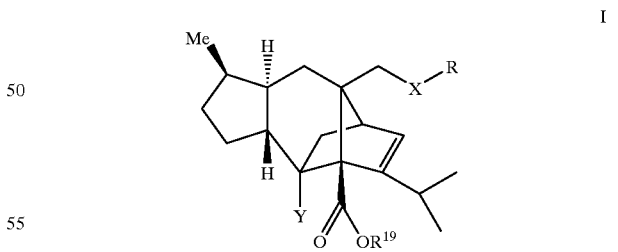

and pharmaceutically acceptable salts or solvates thereof, wherein X is S, SO, SO$_2$, or S(O) (NR$^1$) and Y is CHO or CN.

R is selected from H, C(=O)OR$^1$, C(=O)NR$^2$R$^3$, C(=O)R$^4$, (CH$_2$)$_m$(C=O)R$^4$, CH(R$^2$)OR$^5$, CH(R$^2$)SR$^5$, C(R$^6$)(R$^7$)(R$^8$),

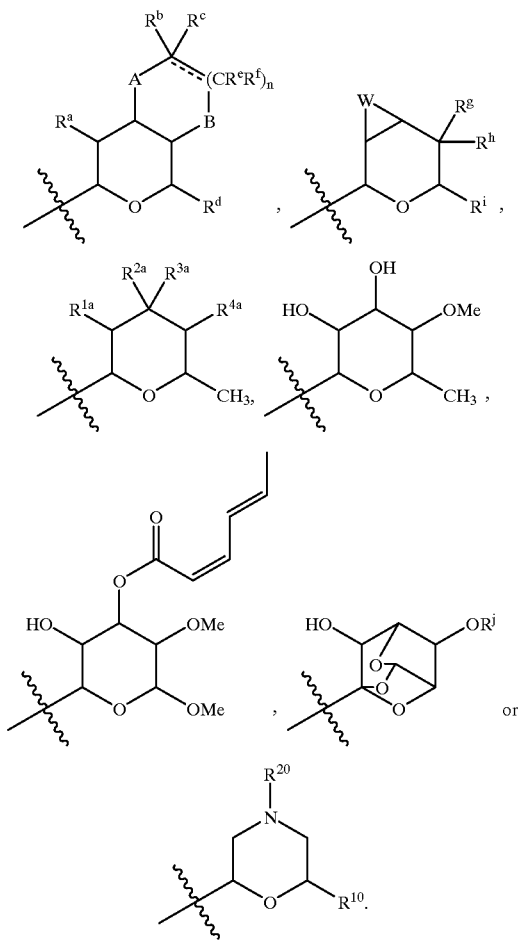

R[1] is $C_1$–$C_{14}$ alkyl, $C_2$–$C_{14}$ alkenyl, $C_2$–$C_{14}$ alkynyl, $C_3$–$C_{20}$ cycloalkyl, aryl or aryl-$C_1$–$C_6$ alkyl-.

R[2] and R[3] are independently H or R[1], R[4] is H, R[1], or —(CH$_2$)$_m$NR[2]R[3].

R[5] is H, R[1], or —(CH$_2$)$_x$O(CH$_2$)$_y$H.

R[6] is H, $C_{1-14}$ alkyl, aryl, aryl -$C_1$–$C_6$ alkyl-, —(CH$_2$)$_y$CHR[9](CH$_2$)$_z$H, —(CH$_2$)$_y$C(R[7])=CH(CH$_2$)H, —(CH$_2$)$_y$C(R[7])=CH(CH$_2$)$_m$R[9], —(CH$_2$)$_y$C=C(CH$_2$)$_z$H, —(CH$_2$)$_y$C≡C(CH$_2$)$_m$R[g], or —(CH$_2$)$_y$C(R[7])=CHC≡C(CH$_2$)$_z$H.

R[7] and R[8] are independently H or $C_1$–$C_{14}$ alkyl.

R[9] is OH or NR[2]R[3].

R[10] is H, $C_1$–$C_6$ alkyl, $C_3$–$C_6$ alkenyl, CH$_2$(=O)OR[1], CH$_2$(=O)NR[2]R[3], CH$_2$(=O)R[4], or CH(R[2])OR[5].

R[a] is H, halogen, OH, OR[1], or OC(=O)R[1].

R[b] and R[c] are each independently hydrogen, $C_{1-6}$ alkyl or $C_{1-4}$ alkoxy-$C_{1-4}$ alkyl-, or R[b] and R[c] together with the carbon atom to which they are attached represent C=O, C=S, or $C_{3-8}$ cycloalkyl.

R[d] is hydrogen or —CH$_2$R[a], where R[a] is defined as above.

R[e] and R[f] are each independently hydrogen, $C_{1-6}$ alkyl or $C_{1-4}$ alkoxy-$C_{1-4}$ alkyl-, or R[e] and R[f] together with the carbon atom to which they are attached represent C=O, C=S, or $C_{3-8}$ cycloalkyl.

A and B are each independently oxygen, sulfur, or CR[11]R[12] in which R[11] and R[12] are each independently hydrogen, $C_{1-6}$ alkyl, $C_{1-4}$ alkoxy, or $C_{1-4}$ alkoxy-$C_{1-4}$ alkyl-, or R[11] and R[12] together with the carbon atom to which they are attached represent C=O, C=S, $C_{3-8}$ cycloalkyl, or C=CHR[13] where R[13] represents hydrogen or $C_{1-4}$ alkyl; or when A or B is oxygen and n is zero then —B—CR[b]R[c] or —A—CR[b]R[c] respectively may also represent —N=CR[c]— or —NR14—CR[b]R[c]— in which CR[b] and CR[c] are C=O and R[14] is $C_{1-4}$ alkyl or an acyl group COR[15] where R[15] is $C_{1-6}$ alkyl or when B is oxygen and n is zero A may represent the group CR[13] in which CR[13] has the meanings defined above which is attached to the pyran ring by a double bond.

R[g] is hydrogen, halogen, azido, $C_{1-6}$ alkyl, hydroxy, $C_{1-6}$ alkoxy, $C_{1-6}$ alkoxy substituted by one or two hydroxy groups or a ketal thereof or one or two $C_{1-3}$ alkoxy groups, aryl-$C_{1-4}$ alkoxy, $C_{3-6}$ alkenyloxy, a group OCOR[16] in which R[16] is aryl $C_{1-4}$ alkoxy or a $C_{1-10}$ alkyl group optionally containing one or two double bonds or $C_{1-6}$ alkoxycarbonyl-$C_{1-4}$ alkoxy, and R[h] represents hydrogen or R[g] and R[h] may, together with the carbon atom to which they are attached, represent C=O or C=CH$_2$. R[i] is CH$_2$R where R[17] is hydrogen, hydroxyl, $C_{1-14}$ alkoxy, or a group OCOR[18] wherein R[18] is $C_{1-4}$ alkyl. R[j] is O(CO)CH$_3$ or CH$_3$. W is oxygen, sulfur, or CH$_2$. The dotted line in group (i) denotes the optional presence of an additional bond.

R[1a] is hydrogen, halogen, hydroxy, or $C_{1-4}$ alkoxy.

R[2a] is hydrogen, halogen, hydroxy, $C_{1-10}$ alkoxy, $C_{1-10}$ alkylthio, $C_{1-6}$ alkoxy-$C_{1-4}$ alkoxy, aryl-$C_{1-6}$ alkyloxy, aryl-$C_{3-6}$ alkenyloxy, azido, NR[5a]COR[5a] in which each R[5a] is independently hydrogen or $C_{1-6}$ alkyl, OR[6a] in which R[6a] is a cyclic ether containing four to eight atoms linked to the oxygen atom via a ring carbon atom adjacent to the ring oxygen atom or a group Z[a]C=O—Z[b]—R[7a] where Z[a] is oxygen, sulfur, or NH, Z[b] is either a bond, an oxygen atom, or a moiety NR[8a] in which R[8a] is hydrogen or $C_{1-6}$ alkyl, and R[7a] is $C_{1-10}$ alkyl optionally containing one or two double bonds, aryl, aryl-$C_{1-4}$ alkyl, aryl-$C_{2-4}$ alkenyl, halo-$C_{1-6}$ alkyl, or $C_{1-6}$ alkoxy- $C_{1-4}$ alkyl.

R[3a] represents hydrogen, or R[2a] and R[1a] together with the carbon atom to which they are attached represent C=O or C=NOR[9a] in which R[9a] is $C_{1-6}$ alkyl.

R[4a] is hydroxyl, $C_{1-6}$ alkoxy or O(C=O)R[7a] in which R[7a] is defined as above.

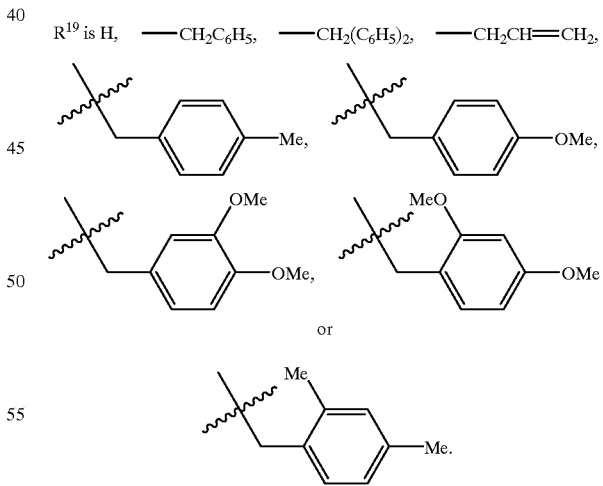

R[20] is $C_{1-6}$ alkyl, $C_{1-6}$ alkoxy, phenoxy, $C_{3-6}$ alkenyloxy optionally substituted by one or two halogen atoms, $C_{1-4}$ alkoxy substituted by an optionally substituted phenyl group, $C_{3-8}$ alkynyl, $C_{3-6}$ alkenyl optionally substituted by $C_{1-4}$ alkoxy or one or two halogen atoms, optionally substituted phenyl, optionally substituted $C_{3-7}$ cycloalkyl, $C_{5-7}$ cycloalkenyl, $C_{2-4}$ alkyl substituted by $C_{1-4}$ alkoxy, $C_{1-4}$ alkylthio or halogen, $C_{1-4}$ alkyl substituted by $C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, or 1 or 2 optionally substituted phenyl groups, or methyl substituted by $C_{1-6}$ alkanoyl or benzoyl.

In addition, n is 0 or 1, m is 1–6, x is 2–6, y is 0–6 and z is 0–6.

This invention also relates to a pharmaceutical composition comprising an antifungal effective amount of a compound of the present invention, or a pharmaceutically acceptable salt, solvate or prodrug thereof, and a pharmaceutically acceptable carrier.

This invention further relates to a method for treating fungal infection in a mammalian host comprising the administration, to a host in need of such treatment, an antifungal effective amount of a compound of formula I.

DETAILED DESCRIPTION OF THE INVENTION

In the present invention, unless otherwise specified the following definitions apply.

The numbers in the subscript after the symbol "C" define the number of carbon atoms a particular group can contain. For example, "$C_1$–$C_8$" means a substituent containing from one to eight carbon atoms.

As used herein, the term "alkyl" means a saturated, straight chain or branched monovalent hydrocarbon radical having the stated number of carbon atoms. Examples of such alkyl radicals include methyl, ethyl, n-propyl, isopropyl, iso-butyl, sec-butyl, t-butyl, n-hexyl, etc.

Haloalkyl refers to an alkyl radical that is substituted with one or more halo radicals, such as trifluoromethyl.

Halo means chloro, bromo, iodo or fluoro radicals.

The term "alkoxy" means any of methoxy, ethoxy, n-propoxy, isopropoxy and the like.

The term "alkenyl" means a partially-saturated, straight chain or branched monovalent hydrocarbon radical having the stated number of carbon atoms and is typified by groups such as vinyl, crotonyl and isopentyl.

The term "alkynyl" means a straight or branched carbon chain having at least one carbon—carbon triple bond and the indicated number of carbon atoms, e.g. acetylenyl, propargyl, butynyl, 1,3-pentadiynyl, and the like.

The term "cycloalkyl" means a saturated carbocycle containing one or more rings and having the indicated number of ring carbon atoms, e.g. cyclopropyl, cyclobutyl, cyclopentyl, cyclohexyl, etc.

The term "aryl" as a group or part of a group means phenyl or heteroaryl each optionally substituted by one to three groups independently selected from halogen, hydroxyl, $C_{1-6}$ alkyl, $C_{1-6}$ alkoxy, or $C_{1-4}$ alkoxycarbonyl. The heteroaryl group may be a 5- or 6-membered heteroaromatic ring containing one or more heteroatoms selected from nitrogen, oxygen, and sulfur. Suitable examples of heteroaryl groups include furanyl, oxazolyl, iso-oxazolyl, imidazolyl, pyrazolyl, thiazolyl, isothiazolyl, oxadiazolyl, thiadiazolyl, triazolyl, pyridyl, pyrimidyl, pyridazinyl, pyrazinyl, triazinyl, furyl, thienyl, and pyrrolyl. The term "optionally substituted 5 or 6 membered heteroaryl" as used in connection with substituent $R^{20}$ means a heteroaryl group as defined above optionally substituted by one or two groups selected from $C_{1-4}$ alkyl, hydroxyalkyl (e.g. hydroxymethyl), acyloxyalkyl (e.g. acetoxymethyl) or halogen.

The term "optionally substituted phenyl" as a group or part of a group includes phenyl or phenyl substituted by one or two groups which may be the same or different and selected from $C_{1-4}$ alkyl, halogen, hydroxy, $C_{1-4}$ alkoxy, methylenedioxy or trifluoromethyl.

The term "optionally substituted $C_{3-7}$ cycloalkyl" as a group or part of another group is a cyclopropyl, cyclobutyl, cyclopentyl, cyclohexyl or cycloheptyl group which may be substituted by one or two methyl, methoxy, hydroxy or phenyl groups or may be fused to a phenyl group to form a bicyclic ring system linked to the rest of the molecule via a carbon atom in with the cycloalkyl ring, e.g. indanyl or tetrahydronaphthyl.

Examples of preferred $R^{20}$ groups include $C_{1-6}$ alkyl (methyl, ethyl, propyl, isopropyl, n-butyl, 1-methylpropyl, t-butyl, 1-ethylpropyl, pentyl, 3-methybutyl, 3,3-dimethylbutyl), $C_{1-4}$ alkoxy (methoxy, ethoxy), $C_{1-4}$ alkoxy substituted by phenyl (phenylmethoxy), phenoxy, $C_{2-4}$ alkyl substituted by $C_{1-4}$ alkoxy (methoxyethyl, ethoxyethyl, ethoxypropyl, isopropoxypropyl), $C_{2-4}$ alkyl substituted by $C_{1-2}$ alkylthio (ethylthioethyl), $C_{2-4}$ alkyl substituted by halogen (2-chloroethyl, 2,2,2-trifluoroethyl), $C_{1-4}$ alkyl substituted by cyano (cyanomethyl or cyanoethyl), $C_{1-4}$ alkyl substituted by propadienyl (2,3-butadienyl) optionally substituted $C_{3-6}$ cycloalkyl e.g. [(cyclopropyl optionally substituted by phenyl), cyclobutyl, cyclopentyl, cyclohexyl (optionally substituted by hydroxy or alkyl e.g. methyl), indanyl or tetrahydronaphthyl], phenyl, $C_{1-4}$ alkyl substituted by optionally substituted furanyl (e.g. furanylmethyl, hydroxymethylfuranylmethyl, acetoxymethylfuranylmethyl), pyridyl (e.g. pyridylmethyl or pyridylethyl), optionally substituted pyrrole e.g. (1-methylpyrrolemethyl) optionally substituted thiazolyl e.g. (thiazolylmethyl) optionally substituted imidazole e.g. N-hydroxymethylimidazolylmethyl, $C_{1-4}$ alkyl substituted by $C_{1-2}$ alkoxycarbonyl (e.g. methoxycarbonylethyl, 1-methoxycarbonyl-2-methylpropyl), aralkyloxycarbonyl (e.g. benzyloxycarbonylmethyl) or aryloxycarbonyl (e.g. phenoxy carbonylmethyl), $C_{1-4}$ alkyl substituted by optionally substituted $C_{3-6}$ cycloalkyl (e.g. cyclopropylmethyl, cyclohexylmethyl, cyclohexylethyl, 1-cyclohexylethyl), $C_{3-6}$ alkenyl (e.g. allyl, 2-methylallyl, 3-methylallyl, 3,3-dimethylallyl), $C_{3-6}$ alkenyl substituted by alkoxy e.g. 2-methoxyallyl, 2-methoxymethylallyl, $C_{3-6}$ alkenyl substituted by 1 or 2 halogen atoms selected from chlorine, bromine or fluorine e.g. (2-fluoromethylallyl, 2-chloroallyl, 2-bromoallyl, 2-fluoroallyl, 3-fluoroallyl, 3,3-difluoroallyl), $C_{3-6}$ alkenyloxy optionally substituted by halogen (e.g. allyloxy, 2-chloroallyloxy), $C_{1-4}$ alkyl substituted by 1 or 2 optionally substituted phenyl groups [wherein the optional substituent in the phenyl ring is selected from 1 or 2 halogen atoms, e.g. chlorine or fluorine, trifluoromethyl, hydroxy, methoxy or methylenedioxy; (examples of such groups include optionally substituted benzyl e.g. benzyl, 4 methoxybenzyl, 4-trifluoromethylbenzyl, difluorobenzyl such as 2,6-difluorobenzyl, 3,4-difluorobenzyl, 2,5-difluorobenzyl, or 2,4-difluorobenzyl, methylenedioxybenzyl, 1-phenyl ethyl, phenethyl (optionally substituted by 1 or 2 hydroxyl groups, methoxy, halogen e.g. fluorine or chlorine), phenylpropyl or diphenylmethyl)], $C_{3-8}$ alkynyl e.g. 2-propynyl, 1-methyl-2-propynyl, 3-methyl-2-propynyl, $C_{5-7}$ cycloalkenyl e.g. 1-cyclohexen-3-yl, or methyl substituted by acetyl or benzoyl.

More preferred $R^{20}$ groups include methyl, ethyl, propyl, isopropyl, butyl, 1-methylpropyl, 3-methylbutyl, methoxy, cyclopropyl, allyl, 2-methylallyl, allyl substituted by halogen, e.g. 2-chloroallyl, 2-fluoromethyallyl, 2-bromoallyl, or 3,3-difluoroallyl), phenyl, ethylthioethyl, methoxyethyl, benzyl, furylmethyl, 2,6-difluorophenylmethyl, 3,4-difluorophenylmethyl, 3,5-difluorophenylmethyl, 3,4-methylenedioxyphenylmethyl, 4-methoxyphenylmethyl, 1-phenylethyl, propynyl, 2,3-butadienyl, allyloxy and 2-chloroallyoxy.

In a preferred embodiment, the present invention relates to antifungal compounds having the following structural formula:

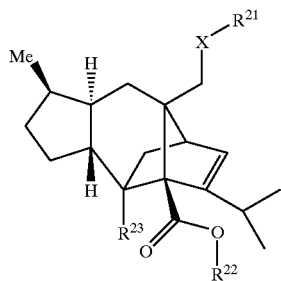

II

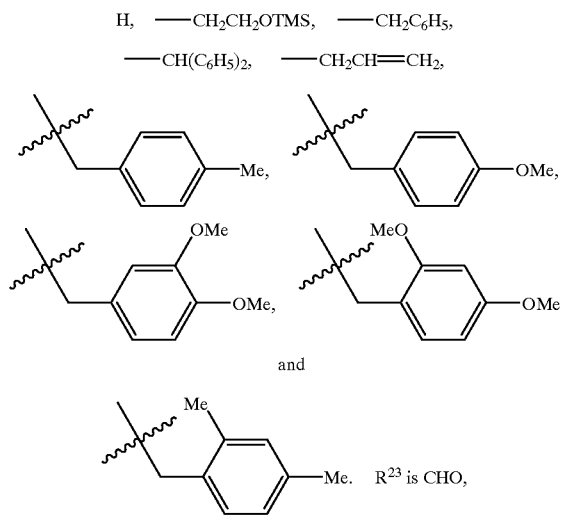

and pharmaceutically acceptable salts or solvates thereof, wherein X is S, S(O) or S(O)$_2$, and R$^{21}$ is selected from C$_1$–C$_8$ alkyl or C$_1$–C$_8$ alkenyl, wherein R$^{21}$ is optionally substituted with C$_1$–C$_2$ alkyl or C$_1$–C$_2$ alkoxy, oxazolinyl, isoxazolidinyl, methyl-oxazolinyl, or methyl-isoxazolidinyl. R$^{22}$ is selected from

H, —CH$_2$CH$_2$OTMS, —CH$_2$C$_6$H$_5$, —CH(C$_6$H$_5$)$_2$, —CH$_2$CH=CH$_2$,

CN, CH(OR$^{24}$)$_2$, CH(SR$^{24}$)$_2$, CH=N(OR$^{24}$), CH=N(NR$_2^{24}$), CH=CR$^{24}$R$^{24}$, C(=O)R$^{24}$, CH$_2$OR$^{24}$; and R$^{24}$ is H or C$_1$–C$_6$ alkyl.

For the compounds of structural formula II, it is preferred that R$^{22}$ is H. It is also preferred that R$^{23}$ is CHO. It is further preferred that X is S or S(O)$_2$. In an even more preferred embodiment, R$^{22}$ is H, R$^{23}$ is CHO, and X is S or S(O)$_2$.

In yet a more preferred embodiment, the compounds of the present invention have the following structural formula:

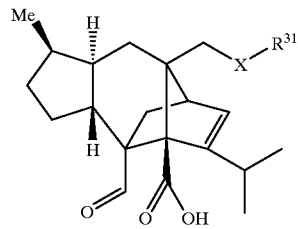

III and pharmaceutically acceptable salts or solvates thereof, wherein X is S, S(O) or S(O)$_2$ and R$^{31}$ is C$_1$–C$_5$ alkyl or C$_2$–C$_5$ alkenyl.

Suitable pharmaceutically acceptable salts of the compounds of the present invention include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine), procaine, ethanolamine, diethanolamine, N-methylglucosamine and tri(hydroxymethyl)ethylamine salts, and amino acid salts (e.g. lysine and arginine salts).

By virtue of its acidic moiety, where applicable, a compound of the present invention forms salts by the addition of a pharmaceutically acceptable base. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)-aminomethane and tetramethylammonium hydroxide and basic amino aids such as lysine, arginine and N-methylglutamine. These salts may be prepared by methods known to those skilled in the art.

As used herein, the term "mammal" shall refer to the Mammalia class of higher vertebrates. The term "mammal" includes, but is not limited to, mice, dogs, cats, rats, hamsters, guinea pigs, cows, horses, apes and humans.

The preferred mammal, for treatment by compounds of the present invention, is a human.

The term "treating" as used herein includes prophylaxis of the named condition or amelioration or elimination of the condition once it has been established.

As used herein, the term "therapeutically effective amount" refers to an amount of a compound which is effective, upon single or multiple dose administration or continuous infusion to the patient, at a minimum, in controlling fungal growth or infection.

As used herein the term "controlling" as referring to fungal growth or infection refers to slowing, interrupting, arresting or stopping of the spread of the given infection and does not necessarily refer to a total elimination of the infection.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

This invention also encompasses pharmaceutically acceptable prodrugs of the compounds of the present invention. Prodrugs are derivatives of the compounds of the invention which have chemically or metabolically cleavable groups and become, by solvolysis or under physiological conditions, the compounds of the invention which are pharmaceutically active in vivo. A prodrug of a compound of may be formed in a conventional manner with a functional group of the compounds such as with an amino, hydroxy or carboxy group. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or (alkoxycarbonyl)oxy)alkyl esters. When a compound of contains a carboxy group, it can form physiologically hydrolyzable esters which serve as prodrugs by being hydrolyzed in the body to yield compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl benzyl, 4-methoxybenzyl, indanyl, phthalilyl, methoxymethyl, $C_{1-6}$ alkanoyloxy-$C_{1-6}$ alkyl, e.g. acetoxymethyl, pivaloyloxymethyl or propionyloxymethyl, $C_{1-6}$ alkoxycarbonyloxy-$C_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters are prepared by conventional techniques known in the art.

Certain compounds of the present invention may also exist in different stable conformational forms which may be separable. Torsional asymmetry due to restricted rotation about an asymmetric single bond, for example because of steric hindrance or ring strain, may permit separation of different conformers.

The present invention includes each conformational isomer of compounds of Structural Formula I, II or III and mixtures thereof.

In addition, a compound of Structural Formula I, II, or III, or a salt, solvate or prodrug thereof, may exhibit polymorphism. The present invention also encompasses any such polymorphic form.

Certain compounds of Structural Formula I may contain one or more chiral centers and exist in different optically active forms. When compounds of the present invention contain one chiral center, the compounds exist in two enantiomeric forms. The present invention includes both enantiomers and mixtures of enantiomers such as racemic mixtures. The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present invention may also exist in different stable conformational forms which may be separable. Torsional asymmetry due to restricted rotation about an asymmetric single bond, for example because of steric hindrance or ring strain, may permit separation of different conformers.

The present invention includes each conformational isomer of compounds of the present invention and mixtures thereof.

Certain compounds of the present invention may exist in zwitterionic form and the present invention includes each zwitterionic form of these compounds and mixtures thereof.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers). In the present application, when no specific mention is made of the configuration (cis, trans or R or S) of a compound (or of an asymmetric carbon) then a mixture of such isomers, or either one of the isomers is intended.

The compounds of the present invention are active antifungal agents useful in treating fungal infections in animals, including humans, for the treatment of systemic, topical and mucosal infections caused by *Candida albicans* and *Candida glabrata*. In view of their antifungal activity, compounds of formula I are useful for the treatment of variety of fungal infections in animals, including humans. Such infections include superficial, cutaneous, subcutaneous and systemic mycotic infections such as respiratory tract infections, gastrointestinal tract infections, cardiovascular infections, urinary tract infections, CNS infections, candidiasis and chronic muccocandidiasis and skin infections caused by fungi, cutaneous and mucocutaneous candidiasis, athletes foot, paronychia, fungal nappy rash, candida vulvitis, candida balanitis and otitis externa. They may be used as prophylactic agents to prevent systemic and topical fungal infections. Use as prophylactic agents may be appropriate as part of a selective gut decontamination regimen in the prevention of infection in immunocompromised patients, e.g. AIDS patients, patients receiving cancer therapy or transplant patients.

The treatment involves administering to a patient, in need of such treatment, a compound of the present invention, or a pharmaceutically acceptable salt, solvate or prodrug thereof. It will be appreciated by those skilled in the art that reference herein to treatment extends to prophylaxis as well as the treatment of established infections or symptoms.

The compounds of the present invention are also useful in the preparation and execution of screening assays for antifungal compounds.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice.

The compounds of the present invention are preferably administered as pharmaceutical formulations with one or more pharmaceutically acceptable carriers and, optionally, other therapeutic and/or prophylactic ingredients.

A compound of the present invention can be administered to the mammal in any form or mode which makes the compound bioavailable in effective amounts, including oral and parenteral routes. For example, a compound of can be administered orally, subcutaneously, intramuscularly, intravenously, transdermally, intranasally, rectally, and the like. Oral, intravenous or intramuscular administration is generally preferred. One skilled in the art of preparing formulations can readily select the proper form and mode of administration depending upon the particular characteristics of the compound selected, the disease state to be treated, the stage of the disease, and other relevant circumstances.

The compositions of the invention include those in a form especially formulated for oral, buccal, parenteral, implant, rectal, topical, opthalmic or genito-urinary administration, or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides. Typically, orally administered forms contain from about 1% to about 95% of active ingredient.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurized packs with the use of a suitable propellant, e.g. dichlorodifluoromethane, trichlorofluoromethane, dichlorotetrafluoroethane, carbon dioxide or other suitable gas, or from a nebuliser. In the case of a pressurized aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilized components. Pour-ons may, for example, be formulated for veterinary use in oils containing organic solvents, optionally with formulatory agents, e.g. stabilizing and solubilizing agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilizing and/or dispersing agents.

Transdermal administration may be affected by the design of a suitable system which promotes absorption of the active compound through the skin and would typically consist of a base formulation enclosed within an adhesive stick-on patch comprising backing films, membranes and release liners.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

A therapeutically effective amount of a compound of the present invention can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual mammal; the particular compound administered; the bioavailability characteristics of the preparation administered; the dose regimen selected; the use of concomitant medication; and other relevant circumstances.

When the compositions comprise dosage units, each unit will preferably contain 0.001 mg to 1000 mg of active ingredient where a compound of the invention is to be administered orally. A therapeutically effective amount of a compound of the present invention, for treatment of a human, is expected to vary from 0.001 mg/kg/day to about 5000 mg/kg/day of active ingredient which may be administered in one or more daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations.

The compounds of the present invention may be prepared according to the following scheme.

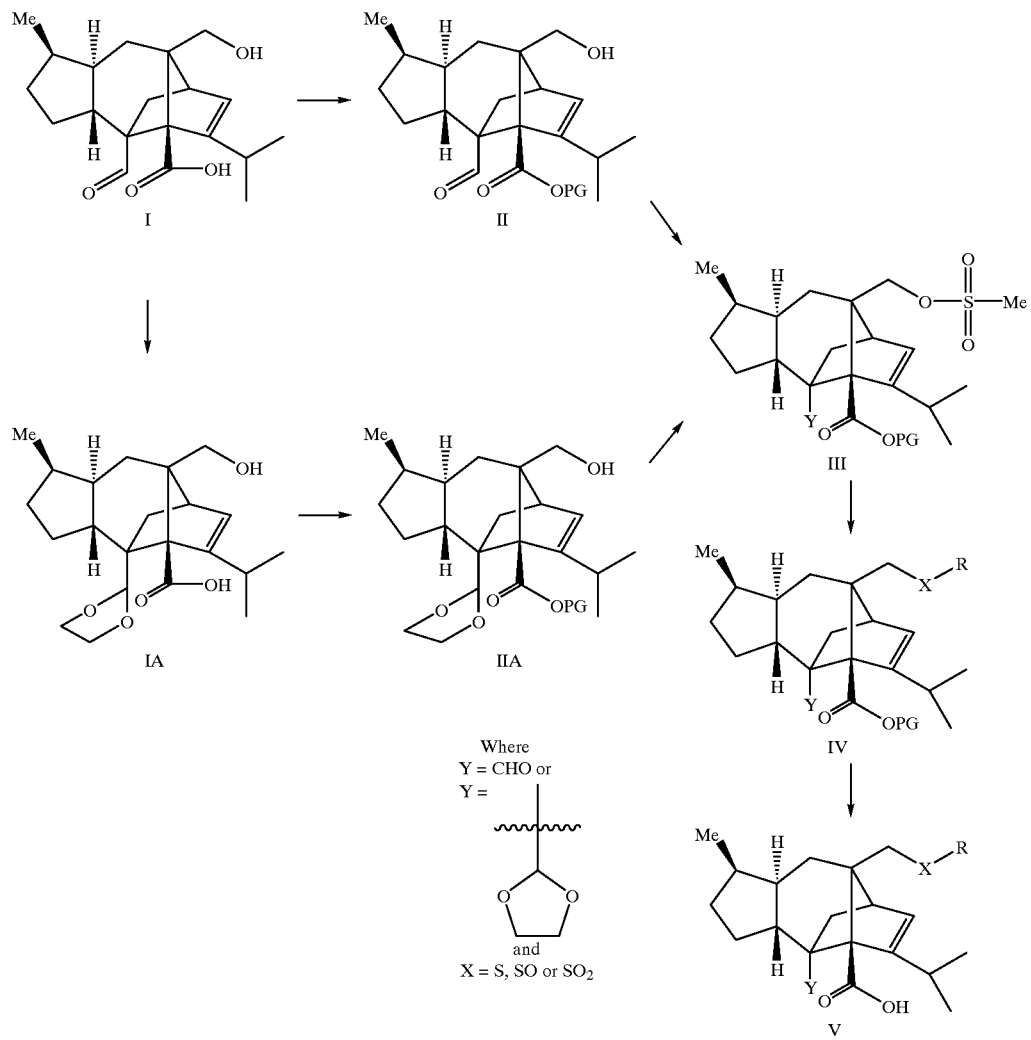

The starting material, Compound I which is also known as sordaricin, can be prepared from sordarin by treatment with concentrated hydrochloric acid. As disclosed in International Application WO96/14326, sordaricin can also be obtained from fermentation of a mutant derived from *Sordaria araneosa* NRRL3196, and by biotransformation of sordarin using a Coryneform species Sordarin can be obtained by cultivation of *Sordaria araneosa* NRRL3196 (also deposited with the ATCC as ATCC 36386) according to the procedure described in GB 1,162,027 or in WO96/14326. Sordarin can also be isolated from the fermentation of *Rosellinia subiculata* (ATCC 74386) or an unidentified fungus (ATCC 74387). Both cultures were deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure. The preparation of Compound I from sordarin has also been reported in the literature reference *Helv. Chim. Acta* 54, 4, 1187 (1971).

Optionally, the aldehyde of Compound I is then protected, such as by using ethylene glycol in the presence of catalytic amounts of a protic acid (i.e., pyridinium para-toluenesulfonic acid) in a solvent such as methylene chloride or methanol, to form the ethylene ketal Compound IA.

The carboxylic acid of Compound I or IA may then be esterified with an appropriate protecting group (denoted as "PG" and in accordance with the state of the art; see, for example, *Protecting Groups in Organic Synthesis*, by T. W. Greene and P. G. M. Wuts, Wiley Interscience, 1991), to form Compound II or IIA, respectively, by reaction with an alkyl halide in the presence of an inorganic base such as sodium bicarbonate, or an isourea as described in the literature [*Synthesis*, 561 (1979)], or with a diazoalkane such as diazomethane or diphenyldiazomethane. The preparation of Compound II, in for the above synthetic sequence, has also been previously reported in Bioorganic Med. Chem. Lett. (1998), vol. 8, pp. 2269–2272.

Compound IIA may also be prepared with other suitable aldehyde protecting group, with the carboxylic acid masked with an appropriate protecting group.

Compound III is then prepared from Compound II or IIA by activating Compound II or IIA for displacement with an activating agent such as methanesulfonyl chloride, p-toluenesulfonyl chloride, or trifluoromethanesulfonic anhydride in the presence of an amine base such as triethylamine or pyridine in an aprotic solvent such as dichloromethane.

Compound IV is then prepared from Compound III by reacting the leaving group with the appropriate sulfur nucleophile in the presence of a strong base such as sodium hydride in a polar aprotic solvent such as dimethylformamide (DMF). The displacement may be performed at elevated temperatures to drive the reaction to completion.

The final product, Compound V, is then formed from Compound IV by standard deprotection methods.

EXEMPLIFICATION

The following examples illustrate the invention, but are not intended as a limitation thereof. The abbreviations used in the examples and in the present specification are conventional abbreviations well-known to those skilled in the art.

Preparation of the Sordaricin ethylene ketal: [1R-(1α,3aβ, 4β,4aβ,7β,8aα,8aβ)]-8a-hydroxymethyl-4-(1,3-dioxolan-2-yl)-4,4a,5,6,7,7a,8,8a-octahydro-7-methyl-3-(1-methylethyl)-1,4-methano-s-indacene-3a(1H)-carboxylic acid

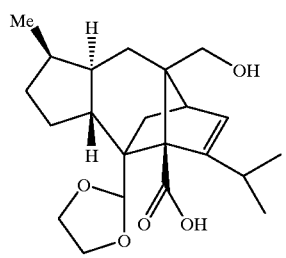

To a solution of sordaricin (0.50 g, 1.5 mmol, 1.0 equiv) in 5 mL methanol was added 3 mL ethylene glycol and 0.63 mL trimethylorthoformate. Pyridium p-toluenesulfonic acid (0.38 g, 1.5 mmol, 1.0 equiv) was added in one portion as a solid, and the resultant homogeneous solution was stirred at ambient temperature overnight. The volatiles were then removed under reduced pressure, and the residue was dissolved in EtOAc and washed sequentially with saturated NH$_4$Cl, water, and brine. The organic layer was dried over Na$_2$SO$_4$, filtered, and concentrated in vacuo. The product was then purified by flash chromatography (30–50% EtOAc in hexanes) to afford the title compound in quantitative yield.

Partial $^1$H NMR (CDCl$_3$): δ5.98 (1H, m), 4.62 (1H, s), 4.11 (1H, d, J=12.0 Hz), 3.83–4.16 (4H, m), 3.34 (1H, d, J=12.0 Hz), 1.08 (3H, d, J=6.0 Hz), 1.05 (3H, d, J=6.0 Hz), 0.80 (3H, d, J=6.0 Hz).

Preparation of sordaricin mesylate [1R-(1α,3aβ,4β,4aβ, 7β,7aα,8aβ)]-8a-[[-(methanesulfonyl)oxy]methyl]-4-formyl-4,4a,5,6,7,7a,8,8a-octahydro-7-methyl-3-(1-methylethyl)-1,4-methano-s-indacene-3a(1H)-carboxylic acid, p-methoxybenzyl ester

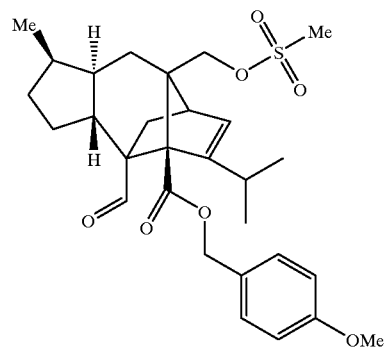

To a solution of [1R-(1α,3aβ,4β,4aβ,7β,7aα,8aβ)]-8a-(hydroxymethyl)-4-formyl-4,4a,5,6,7,7a,8,8a-octahydro-7-methyl-3-(1-methylethyl)-1,4-methano-s-indacene-3a(1H)-carboxylic acid, p-methoxybenzyl ester (0.24 g, 0.053 mmol, 1.0 equiv) in 10 mL CH$_2$Cl$_2$ was added 0.74 mL (0.54 mmol, 10.0 equiv) triethylamine. The solution was cooled to 0° C., and then charged with a solution of methanesulfonyl chloride (0.16 mnL, 0.21 mmol, 4.0 equiv) in 2 mL CH$_2$Cl$_2$. The reaction was allowed to stir at 0° C. for 2 hours, and was then quenched by adding 10 mL saturated NaHCO$_3$. The mixture was extracted with CH$_2$Cl$_2$, and then the combined organic extracts were washed sequentially with water, saturated NH$_4$Cl, and brine. The organic layer was dried over Na$_2$SO$_4$, filtered, and concentrated in vacuo The crude mesylate was then used without further purification. $^1$H NMR (CDCl$_3$, 300 MHz): δ9.59 (s, 1H), 7.33 (d, 2H, J=8.4 Hz), 6.88 (d, 2H, J=8.4 Hz), 6.09 (m, 1H), 5.21 (d, 1H, J=17

Hz), 5.12 (d, 1H, J=11.7 Hz), 4.46 (d, 1H, J=9.5 Hz), 4.30 (d, 1H, J=9.5 Hz), 3.80 (s, 3H), 2.92 (s, 3H), 2.76 (m, 1H), 2.22 (m, 1H).

General procedure for thiol displacement

To a solution of sordaricin mesylate (1.0 equiv) in DMF was added the appropriate thiol (8.0 equiv) followed by NaH (60% dispersion in mineral oil, 16.0 equiv). The reaction was heated to 80° C. for 24–48 hours until no starting material remained. The mixture was then diluted with EtOAc, and the organic layer was washed sequentially with water and brine. The extracts were dried over $Na_2SO_4$, filtered, and concentrated in vacuo. The thioether products were then purified by preparative thin layer silica gel chromatography.

Using the general procedures provided above, the following sordaricin derivatives were synthesized. The reagents used in the following examples to prepare the compounds of the present invention were acquired from the Sigma-Aldrich Corporation.

EXAMPLE 1

[1R-(1α,3aβ, 4β,4aβ,7β,7aα, 8aβ)]-4-formyl-8a-(n-pentylthiomethyl)-4,4a,5,6,7,7a,8,8a-octahydro-7-methylethyl)-1,4-methano-s-indacene-3a(1H)-carboxylic acid

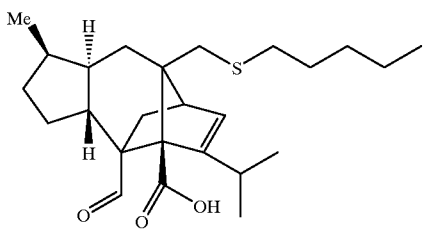

The general procedure described above was followed using 1-pentanethiol to afford the title compound. $^1$H NMR ($CDCl_3$, 300 MHz): δ9.63 (s, 1H), 6.10 (m, 1H), 3.03 (d, 1H, J=12.5 Hz), 2.80 (m, 1H), 2.68 (d, 1H, J=12.5 Hz). LRMS: 417.23 (M–H).

EXAMPLE 2

[1R-(1α, 3aβ,4β, 4aβ,7β,7aα,8aβ)]-4-formyl-8a-(i-pentylthiomethyl)-4,4a,5,6,7,7a,8,8a-octahydro-7-methyl-3-(1-methylethyl)-1,4-methano-s-indacene-3a(1H)-carboxylic acid

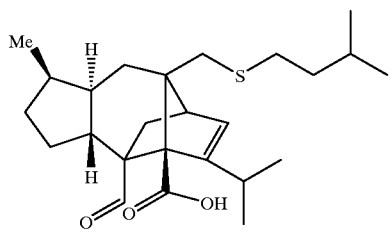

The general procedure described above was followed using 3-methyl-1-butanethiol to afford the title compound. $^1$H NMR ($CDCl_3$, 300 MHz): δ9.63 (s, 1H), 6.10 (m, 1H), 3.01 (m, 1H), 2.80 (m, 1H), 2.68 (m, 1H). LRMS: 417.26 (M–H).

EXAMPLE 3

[1R-(1α,3aβ,4β, 4aβ, 7β,7aα,8aβ)]-4-formyl-8a-(n-hexylthiomethyl)-4,4a,5,6,7,7a,8,8a-octahydro-7-methyl-3-(1-methylethyl)-1,4-methano-s-indacene-3a(1H)-carboxylic acid

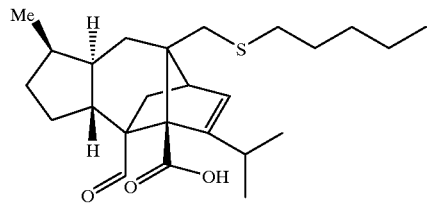

The general procedure described above was followed using 1-hexanethiol to afford the title compound. $^1$H NMR ($CDCl_3$, 300 MHz): δ9.62 (s, 1H), 6.10 (m, 1H), 3.03 (m, 1H), 2.80 (m, 1H), 2.68 (m, 1H), 2.45 (m, 2H). LRMS: 431.30 (M–H).

EXAMPLE 4

[1R-(1α, 3aβ,4β,4aβ,7β, 7aα,8aβ)]-4-formyl-8a-(i-pentylmethylsulfoxy)-4,4a,5,6,7,7a,8,8a-octahydro-7-methyl-3-(1-methylethyl)-1,4-methano-s-indacene-3a(1H)-carboxylic acid

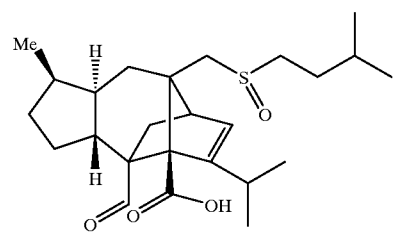

To a solution of the sulfide product of Example 1 (26.1 mg, 0.062 mmol, 1 equiv) in 2 mL MeOH was added monoperoxyphthalic acid magnesium salt (38.5 mg, 0.062 mmol, 1 equiv) at ambient temperature. After 1 h stirring, and additional equivalent of oxidant was added, and the solution was stirred for 4 h until no starting material remained. The reaction mixture was filtered and then purified by reverse phase preparative HPLC to afford the title compound as a mixture of diastereomers (6.4 mg, 24%). $^1$H NMR ($CDCl_3$, 400 MHz): δ9.58 (s, 1H), 6.26 (m, 1H), 3.47 (d, 1H, J=14.0 Hz), 3.34 (d, 1H, J=14.0 Hz), 2.89 (m, 1H), 2.49 (m, 1H), 2.31 (m, 1H). LRMS: 433.32 (M–H).

EXAMPLE 5

[1R-(1α,3aβ,4β,4aβ,7β,7aα,8aβ)]-4-formyl-8a-(i-pentylmethylsulfonyl)-4,4a,5,6,7,7a,8,8a-octahydro-7-methyl-3-(1-methylethyl)-1,4-methano-s-indacene-3a(1H)-carboxylic acid

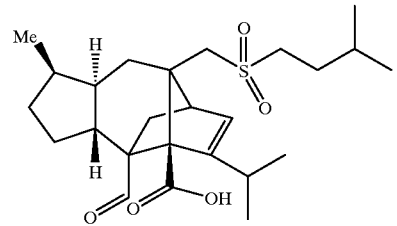

To a 0° C. solution of the sulfide product of Example 1 (28.0 mg, 0.067 mmol, 1.0 equiv) in 2 mL $CH_2Cl_2$ was added mCPBA (25.4 mg, 0.147 mmol, 2.2 equiv) in one portion as a solid. The reaction was allowed to warm to ambient temperature and monitored by TLC until no starting material remained. The heterogeneous reaction was then concentrated in vacuo and purified by reverse phase preparative HPLC to afford 4.2 mg (14%) of the title compound. $^1$H NMR (CDCl$_3$, 400 MHz): β9.61 (s, 1H), 6.19 (m, 1H), 3.55 (d, 1H, J=5.9 Hz), 3.34 (d, 1H, J=13.7 Hz), 3.15 (m, 1H), 2.96 (d, 1H, J=13.7 Hz), 2.77 (m, 1H), 2.62 (m, 1H), 2.40 (m, 1H). LRMS: 449.34 (M−H).

EXAMPLE 6

[1R-(1α,3aβ, 4β,4aβ,7β,7aα,8aβ)]-8a-[[[(3-methylbutyl)]thio]methyl]-4-[(N,N-dimethylamino)imino]-4,4a,5,6,7,7a,8,8a-octahydro-7-methyl-3-(1-methylethyl)-1,4-methano-s-indacene-3a(1H)-carboxylic acid

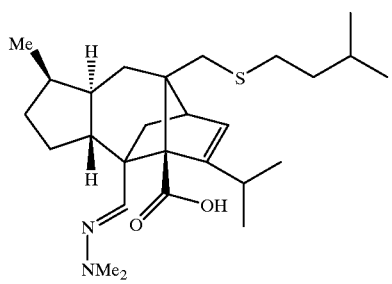

1,1-Dimethylhydrazine (6.4 μL, 0.084 mmol) was added in one portion to a stirred solution of [1R-(1α,3aβ,4β,4aβ,7β,7aα,8aβ)]-8a-[[(3-methylbutyl)-thio]methyl]-4-formyl-4,4a,5,6,7,7a,8,8a-octahydro-7-methyl-3-(1-methylethyl)-1,4-methano-s-indacene-3a(1H)-carboxylate (35 mg, 0.084 mmol), glacial acetic acid (3 drops) and dry pyridine (0.10 mL) in absolute ethanol (1 mL). The mixture was heated to 80° C. for 4h under nitrogen before the ethanol was removed in vacuo and the residue was taken up in ethyl acetate and washed with 1N HCl, brine, dried and concentrated. Purification of the residue by preparative TLC on silica gel (elution with 25% ethyl acetate in hexanes) furnished the title compound (7.9 mg, 21%) as a colorless oil; $^1$H NMR (CDCl$_3$, 300 MHz) δ6.40 (br s, 1H), 6.01 (d, J=3.2 Hz, 1H), 3.07 (d, J=12.4 Hz, 1H), 2.92 (d, J=12.4 Hz, 1H), 2.74 (s, 6H), 2.68-2.66 (m, 1H), 2.49-2.43 (m, 3H), 2.35-2.26 (m, 1H), 2.06-1.98 (m, 3H), 1.90-1.79 (m, 3H), 1.67-1.39 (3 m, 7H), 1.25-1.10 (m, 1H), 1.04 (d, J=6.8 Hz, 3H), 0.98 (d, J=6.8 Hz, 3H), 0.88 (d, J=6.6 Hz, 6H), 0.79 (d, J=6.8 Hz, 3H); LRMS (ESI, m/z, M−H$^-$) 459; LCMS (R$_t$=1.94 min, m/z 461).

EXAMPLE 7

[1R-(1α, 3aβ,4β,4aβ,7β,7aα,8β)]-8a-[[[(2-methyl-5-isoxazolidinyl)methyl]thio]methyl]-4,4a,5,6,7,7a,8,8a-octahydro-7-methyl-3-(1-methylethyl)-1,4-methano-s-indacene-3a(1H)-carboxylic acid

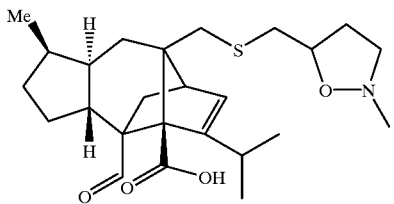

The title compound was made as follows. Paraformaldehyde (0.80 g) was added to a stirred suspension of allyl thioacetate (0.50 g, 4.30 mmol) and N-methylhydroxylamine hydrochloride (0.40 g, 4.73 mmol), triethylamine (0.66 mL) and activated 4 Å powdered molecular sieves (0.5 g) in anhydrous benzene (10 mL) under nitrogen. The mixture was refluxed for 16 h before it was cooled to room temperature and suction-filtered. Following concentration of the mother liquor, the residue was purified by flash chromatography on silica gel (gradient elution with 50% ethyl acetate in hexanes followed by 75% ethyl acetate in hexanes) to afford the title compound (0.67 g, 89%) as a colorless oil; $^1$H NMR (CDCl$_3$, 300 MHz) δ4.40-4.20 (2 m, 1H), 3.30-3.20 (m, 1H), 3.15-3.00 (m, 2H), 2.68-2.63 (m, 4H), 2.50-2.40 (m, 1H), 2.33 (s, 3H), 2.00-1.85 (m, 1H); IR (film, cm$^{-1}$) 2957, 2847, 1692, 1433, 1355, 1136, 1106, 1017, 958, 627; LRMS (ESI, m/z, M+H$^+$) 176; LCMS (R$_t$=0.20 min, m/z, 176). A solution of sodium methoxide in methanol (0.5M, 3.7 mL) was added to a solution of (2-methyl-5-isoxazolidinyl)methyl thioacetate (0.65g, 3.71 mmol) in dry, degassed methanol (5 mL) at room temperature under argon. The mixture was stirred for 2 h before it was concentrated in vacuo and azeotroped with benzene to yield the title compound (0.53 g, 95%) as a reddish-orange foam. This material, sodium (2-methyl-5-isoxazolidinyl)methyl mercaptide, shown below, was used without further purification.

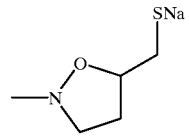

To a stirred solution of [1R-(1α,3aβ,4β,4aβ,7β,7aα,8aβ)]-8a-[[(methanesulfonyl)oxy]methyl]-4-formyl-4,4a,5,6,7,7a,8,8a-octahydro-7-methyl-3-(1-methylethyl)-1,4-methano-s-indacene-3a(1H)-carboxylic acid, p-methoxybenzyl ester (58 mg, 0.12 mmol) in anhydrous dimethylformamide (2 mL) at room temperature under nitrogen was added sodium (2-methyl-5-isoxazolidinyl)methyl mercaptide (45 mg, 0.29 mmol) in one portion. The mixture was heated to 65° C. for 2 h before additional mercaptide (20 mg, 1.1 eq) was added. The mixture was heated further for 1.5 h at 90° C. before it was cooled to room temperature, diluted with ethyl acetate and phosphate buffer (pH=7.2). The organic phase was separated, washed with brine, dried and concentrated. The original aqueous layer was extracted twice more ethyl acetate and the organic extracts were combined and treated likewise as mentioned above. Purification of the residue by preparative HPLC furnished the title compound (37.4 mg, 58%, 2 steps) as a colorless oil; $^1$H NMR (CDCl$_3$, 300MHz) δ9.67 and 9.66 (2 s, 1H), 6.10-6.07 (m, 1H), 5.60 (vbr s, 2H), 4.69-4.64 (m, 1H), 3.49 (s, 1H), 3.15-3.08 (m, 1H), 3.03-2.99 (m, 1H), 2.84-2.71 (m, 4H), 2.62-2.55 (m, 1H), 2.39-2.34 (m, 1H), 2.39-1.87 (series of m, 6H), 1.99 (s, 3H), 1.73-1.70 (m, 2H), 1.28 (d, J=12.7 Hz, 1H), 1.26-1.20 (m, 1H), 1.04 and 1.01 (2 d, J=6.7 and 6.7 Hz, 3H), 0.97 and 0.96 (2 d, J=6.8 and 6.8 Hz, 3H), 0.77 (d, J=6.7 Hz, 3H); LRMS (ESI, m/z, M−H$^-$) 444; LCMS (R$_t$=1.77 min, m/z 446).

EXAMPLE 8

[1R-(1α, 3aβ,4β,4aβ,7β, 7aα,8aβ)]-8a-[[[(3-methyl-2-oxazolinyl)methyl]thio]methyl]-4-formyl-4,4a,5,6,7,7a,8,8a-octahydro-7-methyl-3-(1-methylethyl)-1,4-methano-s-indacene-3a(1H)-carboxylic acid

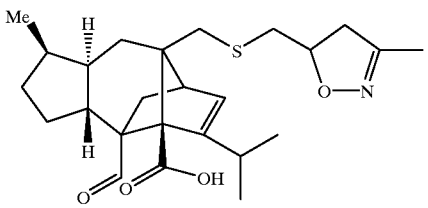

The title compound was made as follows. A solution of nitroethane (0.92 mL, 12.9 mmol) and triethylamine (approx. eight drops) in dry benzene (8 mL) was canulated dropwise to a cold (0° C.) solution of allyl thioacetate (1.0g, 8.6 mmol) and phenylisocyanate (1.86 mL, 17.2 mmol) in anhydrous benzene (12 mL) under nitrogen. The mixture was stirred at room temperature for 1 h before it was refluxed for 2 h. After cooling to room temperature, the precipitates were filtered off and the mother liquor was evaporated to dryness. The residue was taken up in ethyl acetate and washed with saturated sodium bicarbonate solution and brine prior to drying and evaporation. Purification of the residue by flash chromatography on silica gel (gradient elution with 50% ethyl acetate in hexanes followed by 75% ethyl acetate in hexanes) afforded the title compound (0.63 g, 84%) as a colorless oil; $^1$H NMR (CDCl$_3$, 300MHz) δ4.72-4.67 (m, 1H), 3.11 (d, J=5.9 Hz, 2H), 3.01-2.98 (m, 1H), 2.64 (dd, J=17.2, 6.8 Hz, 1H), 2.36 (s, 3H), 1.98 (s, 3H); IR (KBr, cm$^{-1}$) 3431, 2965, 2923, 1689, 1435, 1390, 1354, 1330, 1244, 1148, 1077, 965, 887, 844, 825, 730, 638, 624; LRMS (ESI, m/z, M+H$^+$) 174; LCMS (R$_t$=0.57 min, M+Na$^+$, m/z, 196).

A solution of sodium methoxide in methanol (0.5M, 3.5 mL) was added to a solution of (3-methyl-5-oxazolinyl)methyl thioacetate (0.61 g, 3.52 mmol) in dry, degassed methanol (5 mL) at room temperature under argon. The mixture was stirred for 2 h before it was concentrated in vacuo and azeotroped with benzene to yield the title compound (0.51 g, 95%) as a tan-colored solid. This material, sodium (3-methyl-5-oxazolinyl)methyl mercaptide, shown below, was used without further purification.

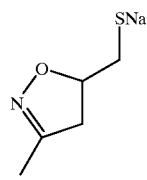

Using sodium (3-methyl-5-oxazolinyl)methyl mercaptide as the nucleophile, the procedure for Example 7 was followed as described above. Obtained 22.6 mg (33%, 2 steps) as a colorless oil; $^1$H NMR (CDCl$_3$, 300 MHz) δ9.67-9.64 (4 s, 1H), 7.62 (v br s, 2H), 6.11-6.08 (m, 1H), 4.60–4.80 (2m, 1H), 4.30-4.10 (m, 1H), 3.22-3.07 (m, 5H), 2.84-2.65 (m, 4H), 2.43-2.34 (m, 2H), 2.07-1.82 (m, 6H), 1.75-1.70 (m, 2H),1.31-1.10 (2 m, 2H), 1.04 (d, J=6.7 Hz, 3H), 0.96 (d, J=6.7 Hz, 3H), 0.78 (d, J=6.4 Hz, 3H); LRMS (ESI, m/z, M-H$^-$) 446; LCMS (R$_t$=1.52 min, m/z 448).

Biological Activity

The in vitro evaluation of the antifungal activity of compounds of the invention was performed on liquid or solid medium by the antifungal two-fold serial dilution technique of determining the minimum inhibitory concentration (MIC) of antifungal agent that inhibited development of growth after 24 to 48 hours of incubation at 37° C. In practice a series of agar plates or broth microdilution panels containing two-fold dilutions of antifungal agent tested were inoculated with a standard culture of a clinically relevant pathogen, e.g. *Candida albicans*. The agar plates or broth microdilution panels were then examined for the presence or absence of growth of the fungus and the appropriate MIC values were noted.

The compounds of the present invention have typically been found to display in vitro antifungal activity against various *Candida Albicans* pathogens, obtained from the American Type Culture Collection, in the range of 0.015 to 32 μg/mL. More specifically, compounds, wherein X is S or SO$_2$, the following antifungal activity has been found:

| | |
|---|---|
| *Candida Albicans* strain A9540 | 0.015 to 1 μg/mL |
| *Candida Albicans* strain A28235 | less than 0.06 to 1 μg/mL |
| *Candida Albicans* strain A28660 | 0.06 to 1 μg/mL |
| *Candida Albicans* strain A29105(efflux def) | 0.008 to 0.5 μg/mL |
| *Candida Albicans* strain A26089(azole res) | less than 0.06 to 2 μg/mL. |

Compounds of the present invention, wherein X is S or SO$_2$, have typically been found to display in vitro antifungal activity against the *Candida Glabrata* A28790(WT) strain in the range of 0.06 to 16 μg/mL.

The invention claimed is:

1. A compound having the structural formula

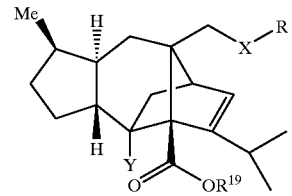

or a pharmaceutically acceptable salt thereof, wherein:

X is S, SO, SO$_2$, or S(O) (NR$^1$);

Y is CHO or CN;

R is selected from H, C(=O)OR$^1$, C(=O)NR$^2$R$^3$, C(=O)R$^4$, (CH$_2$)$_m$(C=O)R$^4$, CH(R$^2$)OR$^5$, CH(R$^2$)SR$^5$, C(R$^6$)(R$^7$)(R$^8$),

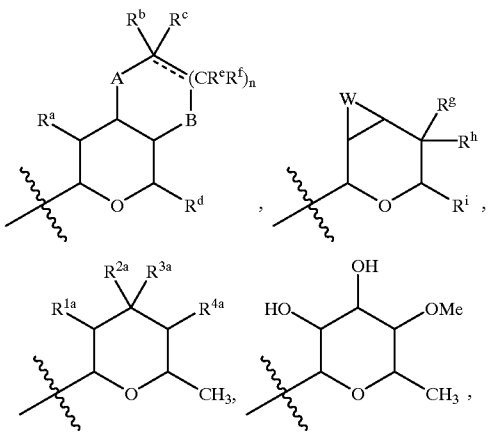

-continued

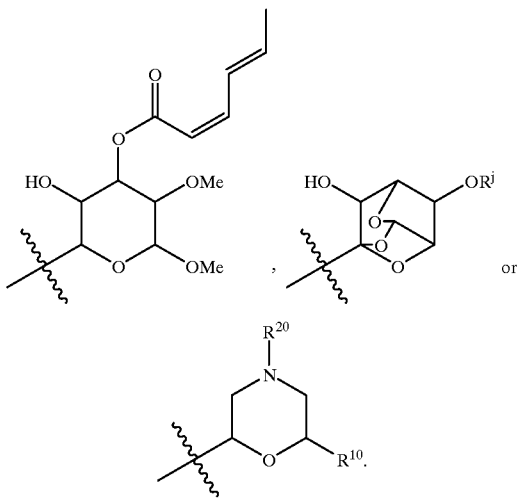

R[1] is $C_1$–$C_{14}$ alkyl, $C_2$–$C_{14}$ alkenyl, $C_2$–$C_{14}$ alkynyl, $C_3$–$C_{20}$ cycloalkyl, aryl or aryl-$C_1$–$C_6$ alkyl-;

R[2] and R[3] are independently H or R[1];

R[4] is H, R[1], or —$(CH_2)_m NR^2 R^3$;

R[5] is H, R[1], or —$(CH_2)_x O(CH_2)_y H$;

R[6] is H, $C_{1-14}$ alkyl, aryl, aryl-$C_1$–$C_6$ alkyl-, —$(CH_2)_y CHR^9 (CH_2)_z H$, —$(CH_2)_y C(R^7)=CH(CH_2)_z H$, —$(CH_2)_y C(R^7)=CH(CH_2)_m R^9$, —$(CH_2)_y C\equiv C(CH_2)_z H$, —$(CH_2)_y C\equiv C(CH_2)_m R^9$, or —$(CH_2)_y C(R^7)=CHC\equiv C(CH_2)_z H$;

R[7] and R[8] are independently H or $C_1$–$C_{14}$ alkyl;

R[9] is OH or $NR^2 R^3$;

R[10] is H, $C_1$–$C_6$ alky, $C_3$–$C_6$ alkenyl, $CH_2(=O)OR^1$, $CH_2(=O)NR^2 R^3$, $CH_2(=O)R^4$, or $CH(R^2)OR^5$;

R[a] is H, halogen, OH, OR[1], or $OC(=O)R^1$;

R[b] and R[c] are each independently hydrogen, $C_{1-6}$ alkyl or $C_{1-4}$ alkoxy-$C_{1-4}$ alky, or R[b] and R[c] together with the carbon atom to which they are attached represent C=O, C=S, or $C_{3-8}$ cycloalkyl;

R[d] is hydrogen or —$CH_2 R^a$, where R[a] is defined as above;

R[e] and R[f] are each independently hydrogen, $C_{1-6}$ alkyl or $C_{1-4}$ alkoxy-$C_{1-4}$ alkyl-, or R[e] and R[f] together with the carbon atom to which they are attached represent C=O, C=S, or $C_{3-8}$ cycloalkyl;

A and B are each independently oxygen, sulfur, or $CR^{11} R^{12}$ in which R[11] and R[12] are each independently hydrogen, $C_{1-6}$ alkyl, $C_{1-4}$ alkoxy, or $C_{1-4}$ alkoxy-$C_{1-4}$ alkyl-, or R[11] and R[12] together with the carbon atom to which they are attached represent C=O, C=S, $C_{3-8}$ cycloalkyl, or C=CHR[13] where R[13] represents hydrogen or $C_{1-4}$ alkyl; or when A or B is oxygen and n is zero then —B—$CR^b R^c$ or —A—$CR^b R^c$ respectively may also represent —N=CR[c]— or NR[14]—$CR^1 R^c$ in which $CR^b$ and $CR^c$ are C=O and R[14] is $C_{1-4}$ alkyl or an acyl group COR[15] where R[15] is $C_{1-6}$ alkyl or when B is oxygen and n is zero A may represent the group CR[13] in which CR[13] has the meanings defined above which is attached to the pyran ring by a double bond;

R[g] is hydrogen, halogen, azido, $C_{1-6}$ alkyl, hydroxy, $C_{1-6}$ alkoxy, $C_{1-6}$ alkoxy substituted by one or two hydroxy groups or a ketal thereof or one or two $C_{1-3}$ alkoxy groups, aryl-$C_{1-4}$ alkoxy, $C_{3-6}$ alkenyloxy, a group OCOR[16] in which R[16] is aryl $C_{1-4}$ alkoxy or a $C_{1-10}$ alkyl group optionally containing one or two double bonds or $C_{1-6}$ alkoxycarbonyl-$C_{1-4}$ alkoxy, and R[h] represents hydrogen, or R[g] and R[h] may, together with the carbon atom to which they are attached, represent C=O or C=$CH_2$;

R[i] is $CH_2 R^{17}$ where R[17] is hydrogen, hydroxyl, $C_{1-14}$ alkoxy, or a group OCOR[18] wherein R[18] is $C_{1-4}$ alkyl;

R[j] is $O(CO)CH_3$ or $CH_3$;

W is oxygen, sulfur, or $CH_2$; the dotted line in group (i) denotes the optional presence of an additional bond;

R[1a] is hydrogen, halogen, hydroxy, or $C_{1-4}$ alkoxy;

R[2a] is hydrogen, halogen, hydroxy, or $C_{1-10}$ alkoxy, $C_{1-10}$ alkylthio, $C_{1-6}$ alkoxy-$C_{1-4}$ alkoxy, aryl-$C_{1-6}$ alkyloxy, aryl-$C_{3-6}$ alkenyloxy, azido, $NR^{5a} COR^{5a}$ in which each R[5a] is independently hydrogen or $C_{1-6}$ alkyl, $OR^{6a}$ in which R[6a] is a cyclic ether containing four to eight atoms linked to the oxygen atom via a ring carbon atom adjacent to the ring oxygen atom or a group $Z^a C=O$—$Z^b$—$R^{7a}$ where $Z^a$ is oxygen, sulfur, or NH, $Z^b$ is either a bond, an oxygen atom, or a moiety $NR^{8a}$ in which R is hydrogen or $C_{1-6}$ alkyl, and R[7a] is $C_{1-10}$ alkyl optionally containing one or two double bonds, aryl, aryl $C_{1-4}$ alkyl, aryl-$C_{2-4}$ alkenyl, halo-$C_{1-6}$ alkyl, or $C_{1-6}$ alkoxy-$C_{1-4}$ alkyl, and R[3a] represents hydrogen, or R[2a] and R[3a] together with the carbon atom to which they are attached represent C=O or C=$NOR^{9a}$ in which R[9a] is $C_{1-6}$ alkyl; and R[4a] is hydroxyl, $C_{1-6}$ alkoxy or $O(C=O)R^{7a}$ in which R[7a] is defined as above;

R[19] is H, —$CH_2 C_6 H_5$, —$CH(C_6 H_5)_2$, —$CH_2 CH=CH_2$,

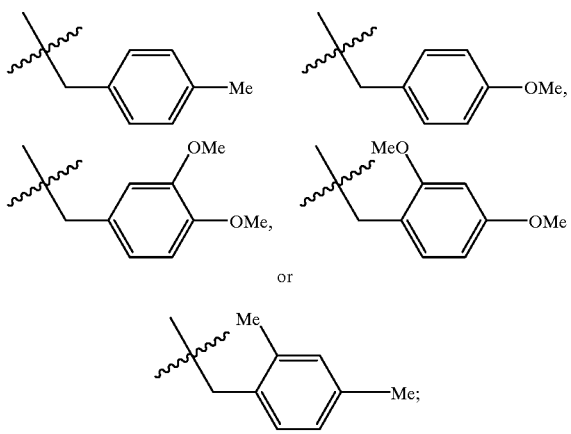

R[20] is $C_{1-6}$ alkyl, $C_{1-6}$ alkoxy, phenoxy, $C_{3-6}$ alkenyloxy optionally substituted by one or two halogen atoms, $C_{1-4}$ alkoxy substituted by an optionally substituted phenyl group, $C_{3-8}$ alkynyl, $C_{3-6}$ alkenyl optionally substituted by $C_{1-4}$ alkoxy or one or two halogen atoms, optionally substituted phenyl, optionally substituted $C_{3-7}$ cycloalkyl, $C_{5-7}$ cycloalkenyl, $C_{2-4}$ alkyl substituted by $C_{1-4}$ alkoxy, $C_{1-4}$ alkylthio or halogen, $C_{1-4}$ alkyl substituted by $C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, or 1 or 2 optionally substituted phenyl groups, or methyl substituted by $C_{1-6}$ alkanoyl or benzoyl;

n is 0 or 1;

m is 1–6;

x is 2–6;

y is 0–6; and z is 0–6.

2. A compound having the structural formula

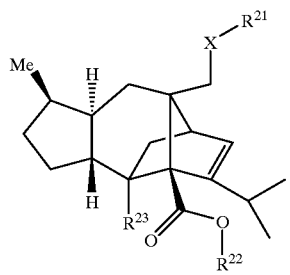

or a pharmaceutically acceptable salt, solvate or prodrug thereof, wherein:

X is S, S(O) or S(O)$_2$;

$R^{21}$ is selected from $C_1$–$C_8$ alkyl or $C_1$–$C_8$ alkenyl, wherein $R^{21}$ is optionally substituted with $C_1$–$C_2$ alkyl or $C_1$–$C_2$ alkoxy, oxazolinyl, isoxazolidinyl, methyl-oxazolinyl, or methyl-isoxazolidinyl;

$R^{22}$ is selected from H, —CH$_2$CH$_2$OTMS, —CH$_2$C$_6$H$_5$, —CH(C$_6$H$_5$)$_2$,—

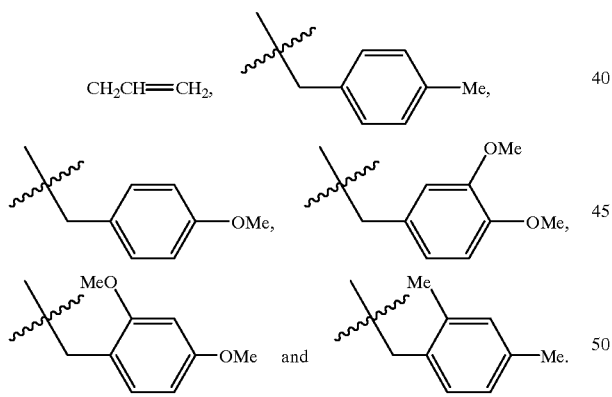

$R^{23}$ is CHO, CN, CH(OR$^{24}$)$_2$, CH(SR$^{24}$)$_2$, CH=N(OR$^{24}$), CH=N(NR$^{224}$), CH=CR$^{24}$R$^{24}$, C(=O)R$^{24}$, CH$_2$OR$^{24}$; and $R^{24}$ is H or $C_1$–$C_6$ alkyl.

3. A compound of claim 2 wherein $R^{22}$ is H.

4. A compound of claim 2 wherein $R^{23}$ is CHO.

5. A compound of claim 2 wherein X is S or S(O)$_2$.

6. A compound of claim 3 wherein:

$R^{22}$ is H;

$R^{23}$ is CHO; and

X is S or S(O)$_2$.

7. A compound having the structural formula

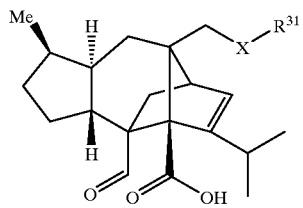

or a pharmaceutically acceptable salt thereof, wherein:

X is S, S(O) or S(O)$_2$; and $R^{31}$ is $C_1$–$C_5$ alkyl or $C_2$–$C_5$ alkenyl.

8. A compound of claim 7 wherein X is X is S or S(O)$_2$.

9. A compound selected from the group consisting of:

(a) [1R-(1α,3aβ,4β,4aβ,7β,7aα,8aβ)]-4-formyl-8a-(n-pentylthiomethyl)-4,4a,5,6,7,7a,8,8a-octahydro-7-methyl-3-(1-methylethyl)-1,4-methano-s-indacene-3a(1H)-carboxylic acid;

(b) [1R-(1α,3aβ,4β,4aβ,7β,7aα,8aβ)]-4-formyl-8a-(i-pentylthiomethyl)-4,4a,5,6,7,7a,8,8a-octahydro-7-methyl-3-(1-methylethyl)-1,4-methano-s-indacene-3a(1H)-carboxylic acid;

(c) [1R-(1α,3aβ,4β,4aβ,7β,7aα,8aβ)]-4-formyl-8a-(n-hexylthiomethyl)-4,4a,5,6,7,7a,8,8a-octahydro-7-methyl-3-(1-methylethyl)- 1,4-methano-s-indacene-3a(1H)-carboxylic acid;

(d) [1R-(1α,3aβ,4β,4aβ,7β,7aα,8aβ)]-4-formyl-8a-(i-pentylmethylsulfoxy)-4,4a,5,6,7,7a,8,8a-octahydro-7-methyl-3-(1-methylethyl)-1,4-methano-s-indacene-3a(1H)-carboxylic acid;

(e) [1R-(1α,3aβ,4β,4aβ,7β,7aα,8aβ)]-4-formyl-8a-(i-pentylmethylsulfonyl)-4,4a,5,6,7,7a,8,8a-octahydro-7-methyl-3-(1-methylethyl)-1,4-methano-s-indacene-3a(1H)-carboxylic acid;

(f) [1R-(1α,3aβ,4β,4aβ,7β,7aα,8aβ)]-8a-[[[(3-methylbutyl)thio]methyl]-4-[(N,N-dimethylamino)imino]-4,4a,5,6,7,7a,8,8a-octahydro-7-methyl-3-(1-methylethyl)-1,4-methano-s-indacene-3a(1H)-carboxylic acid;

(g) [1R-(1α,3aβ,4β,4aβ,7β,7aα,8aβ)]-8a-[[[(2-methyl-5-isoxazolidinyl)methyl]thio]methyl]-4-formyl-4,4a,5,6,7,7a,8,8a-octahydro-7-methyl-3-(1-methylethyl)-1,4-methano-s-indacene-3a(1H)-carboxylic acid; and (h) [1R-(1α,3aβ,4β,4aβ,7β,7aα,8aβ)]-8a-[[[(3-methyl-2-oxazolinyl)methyl]thio]methyl]-4-formyl-4,4a,5,6,7,7a,8,8a-octahydro-7-methyl-3-(1-methylethyl)-1,4-methano-s-indacene-3a(1H)-carboxylic acid, and pharmaceutically acceptable salts, thereof.

10. A pharmaceutical composition, comprising (a) a compound of claim 1, or a pharmaceutically acceptable salt, thereof; and (b) a pharmaceutically acceptable carrier.

11. A pharmaceutical composition, comprising (a) a compound of claim 2, or a pharmaceutically acceptable salt, thereof; and (b) a pharmaceutically acceptable carrier.

12. A pharmaceutical composition of claim 11 wherein $R^{22}$ is H.

13. A pharmaceutical composition of claim 11 wherein $R^{23}$ is CHO.

14. A pharmaceutical composition of claim 11 wherein X is S or S(O)$_2$.

15. A pharmaceutical composition of claim 11 wherein:

$R^{22}$ is H;

$R^{23}$ is CHO; and

X is S or $S(O)_2$.

16. A pharmaceutical composition, comprising
   (a) a compound of claim 7, or a pharmaceutically acceptable salt, thereof; and
   (b) a pharmaceutically acceptable carrier.

17. A pharmaceutical composition of claim 16 wherein X is X is S or $S(O)_2$.

18. A method for the prophylactic or therapeutic treatment of a fungal infection, in an animal in need thereof, comprising the administration to said animal of a therapeutically effective amount a compound of claim 1, 2 or 7 or of a pharmaceutically acceptable salt, thereof.

19. A method of claim 18 wherein said animal is a mammal.

20. A method of claim 19 wherein said mammal is a human.

* * * * *